United States Patent [19]

Kaneko et al.

[11] Patent Number: 4,612,379

[45] Date of Patent: Sep. 16, 1986

[54] PROCESS FOR PRODUCING 1,3-DIOXIN-4-ONE DERIVATIVES

[75] Inventors: Chikara Kaneko; Masayuki Sato; Hiromichi Ogasawara, all of Sendai, Japan

[73] Assignee: Chisso Corporation, Osaka, Japan

[21] Appl. No.: 749,426

[22] Filed: Jun. 27, 1985

[30] Foreign Application Priority Data

Jul. 3, 1984 [JP] Japan ................................ 59-137712

[51] Int. Cl.$^4$ ........................................... C07D 319/06
[52] U.S. Cl. .................................................. 549/274
[58] Field of Search ......................................... 549/274

[56] References Cited

PUBLICATIONS

Sato et al, Chem. Pharm. Bull., 31 (6), pp. 1896–1901 (1983).

Primary Examiner—Dolph H. Torrence
Attorney, Agent, or Firm—Wenderoth, Lind & Ponack

[57] ABSTRACT

A process for producing 1,3-dioxin-4-one derivatives having a lower alkyl group at 2-position and useful as a starting raw material for prostaglandins, with a high yield is provided, which process comprises reacting formyl Meldrum's acid with a lower aliphatic carbonyl compound of 2 to 4 carbon atoms in a solvent containing the carbonyl compound at 100° to 120° C., while portionwise adding the acid into the solvent, the total quantity of the acid added being 0.2 mol or less per liter of the solvent.

5 Claims, 2 Drawing Figures

PROCESS FOR PRODUCING 1,3-DIOXIN-4-ONE DERIVATIVES

BACKGROUND OF THE INVENTION

This invention relates to a process for producing 5,6-unsubstituted-1,3-dioxin-4-one derivatives.

These derivatives are useful compounds as one of starting raw materials for prostaglandins which are physiologically active substances having various pharmacological activities such as blood pressure depression, anti-ulceration, bronchodilation, inhibition of gastric acid secretion, induction of partus, etc.

The derivatives have not heretofore been known at all, but for the first time the present inventors have found a process for producing 2,2-dimethyl-1,3-dioxin-4-one as a compound belonging thereto. Namely, according to the process reported by the present inventors in Chem. Pharm. Bull. 31, (6) 1896 (1983), 2,2-dimethyl-1,3-dioxin-4-one was obtained from formyl Meldrum's acid in the presence of acetone and using a small amount of toluene or xylene as solvent, with a yield of 31%. This formyl Meldrum's acid seems to have a higher reactivity than that of similar acetyl Meldrum's acid. That is, in the case of the latter acid, its thermal decomposition yielded 2,2,6-trimethyl-1,3-dioxin-4-one, whereas in the case of the former acid, its mere heating in the absence of solvent formed only a resinous substance without yielding 2,2-dimethyl-1,3-dioxin-4-one, but when the former acid was heated in a xylene solvent containing acetone, the compound was obtained for the first time. However, its yield was not only low (yield: 31% as described above), but the loss of the raw material acid due to the resin formation was so great that the recovery of the raw material was impossible.

SUMMARY OF THE INVENTION

The object of the present invention is to provide a process for producing 1,3-dioxin-4-one derivatives as important raw material substances in the field of synthetic chemistry.

The present invention has the following main constitution (1) and constitutions (2) and (3) as its preferred embodiments: (1) a process for producing 1,3-dioxin-4-one derivatives having a lower alkyl group at 2-position thereof, which process comprises reacting formyl Meldrum's acid with a lower aliphatic carbonyl compound of 2 to 4 carbon atoms in a solvent containing said carbonyl compound at 100° to 120° C., while portionwise adding said acid into said solvent, the total quantity of said acid added being 0.2 mol or less per liter of said solvent;

(2) a process according to the above item (1) wherein the reaction is carried out under the boiling reflux of said solvent containing said carbonyl compound; and (3) a process according to the above item (1) or (2) wherein said solvent further contains anhydrous aluminum chloride or boron trifluoride as catalyst.

DETAILED DESCRIPTION OF THE PREFERRED EMBODIMENTS

Figure 1:
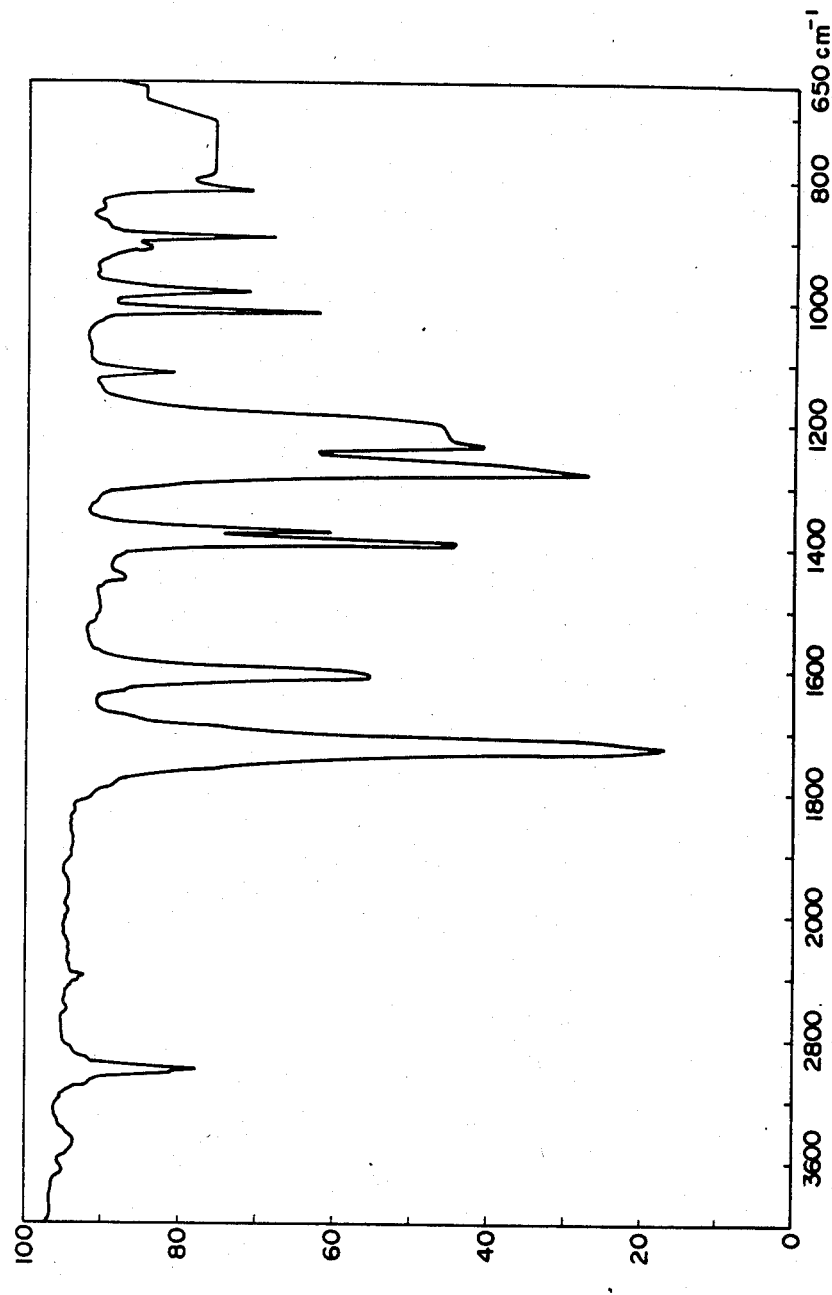
FIG. 1 and FIG. 2 show IR spectra and $^1$H NMR spectra of 2,2-dimethyl-1,3-dioxin-4-one, respectively.

As to the solvent used in the present invention, any of those which are non-protonic and dissolves formyl Meldrum's acid as raw material at the reaction temperature may be used. Examples thereof are toluene, xylene, dioxane, tetrachloroethylene, etc. Among these, toluene is suitable in view of the boiling point of the solvent and the solubility of the solvent in the raw material.

In the process of the present invention, the reaction temperature is suitably 100° to 120° C. If it is lower than 100° C., the reaction proceeds very slow and requires a long time, which results in loss of the product, while if it exceeds 120° C., the quantity of a resinous byproduct increases and the yield lowers.

As to the carbonyl compound used in the present invention, there may be used a compound selected from lower aliphatic aldehydes such as acetaldehyde, propionaldehyde, butyraldehyde or isobutyraldehyde, and lower aliphatic ketones such as acetone or methyl ethyl ketone. When the above aldehydes are used as raw material, it is possible to produce 2-alkyl-1,3-dioxin-4-ones having hydrogen atom at 2-position replaced by methyl group, ethyl group, propyl group or isopropyl group, respectively. On the other hand, when the above ketones are used as raw material, it is possible to produce 2,2-dimethyl-1,3-dioxin-4-one or 2-methyl-2-ethyl-1,3-dioxin-4-one. When the carbonyl compound is acetone, the reaction is expressed by the following equation:

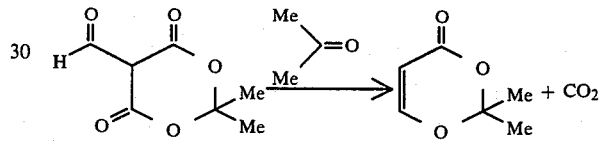

In the present invention, formyl Meldrum's acid is reacted with a carbonyl compound in a reaction solvent containing the carbonyl compound in excess mols of the acid, preferably in 5 to 10 times mols, while the acid is portionwise added to the solvent, the total quantity of the acid added being 0.2 mol or less per liter of the solvent, that is, the reaction is carried out in a liquid phase wherein the reaction raw material is very much diluted, whereby formation of a resinous byproduct is inhibited.

The theoretical elucidation why the resin formation can be inhibited through the reaction under dilution as described above has not yet been sufficiently made, but the reason is presumed as follows:

Although the reaction mechanism is unknown, a process may be considered that at an intermediate step of the reaction, carbon dioxide, acetone and formyl ketene as intermediates are formed from formyl Meldrum's acid, and the formyl ketene reacts with the carbonyl compound to give the objective 1,3-dioxin-4-one derivative. In such a process, since the intermediate formyl ketene is extremely reactive, it is considered that resin formation is promoted in the case of high concentration reaction.

Further, the carbonyl compound to be reacted with the intermediate formyl ketene is preferred to be present in a large quantity in the reaction system, but in order to prevent a condition that reflux of a solvent containing a low boiling carbonyl compound makes it impossible to keep the reaction temperature, the quantity of the low boiling carbonyl compound added has naturally an upper limit. When a low boiling carbonyl compound is used as raw material, the present invention can be performed by using a higher boiling solvent such as xylene, ethylbenzene, etc. Further, when the reaction is carried out under pressure, it is possible to increase the quantity of the low boiling carbonyl compound added, but such a reaction under pressure is not practical when removal of carbon dioxide formed and portionwise addition of formyl Meldrum's acid are taken into account.

The reason of the portionwise addition of formyl Meldrum's acid is that when the concentration of the above intermediate formyl ketene is made as low as possible through the portionwise addition, inhibition of resin formation is effected.

In the present invention, it is also possible to carry out the reaction in the presence of the so-called Lewis acid such as anhydrous aluminum chloride, boron trifluoride etherate, etc. The quantity of the catalyst used is suitably 1/100 to 5/100 of the mols of raw material formyl Meldrum's acid, and the catalyst is added to the solvent containing the carbonyl compound and used. Use of the catalyst makes it possible to shorten the reaction time.

According to the present invention, it is possible to notably improve the yield of 2,2-disubstituted-1,3-dioxin-4-ones, as seen from Examples described below.

EXAMPLE 1

Acetone of special reagent grade (2.9 g, 50 mmols) was added to sufficiently dehydrated toluene of special reagent grade (400 ml), and the mixture was heated in a reaction flask equipped with a reflux condenser. While reflux was continued, crystals of formyl Meldrum's acid (8.6 g, 50 mmols) were added small-portion-wise over about 2 hours, followed by continuing reflux for additional one hour, thereafter distilling off the solvent under reduced pressure while keeping the water bath temperature at 30° C. or lower, and subjecting a remaining oily substance to vacuum distillation to obtain the objective product as a fraction of b.p. 59° C./4 mmHg (3.95 g, yield 62%).

Figure 2:
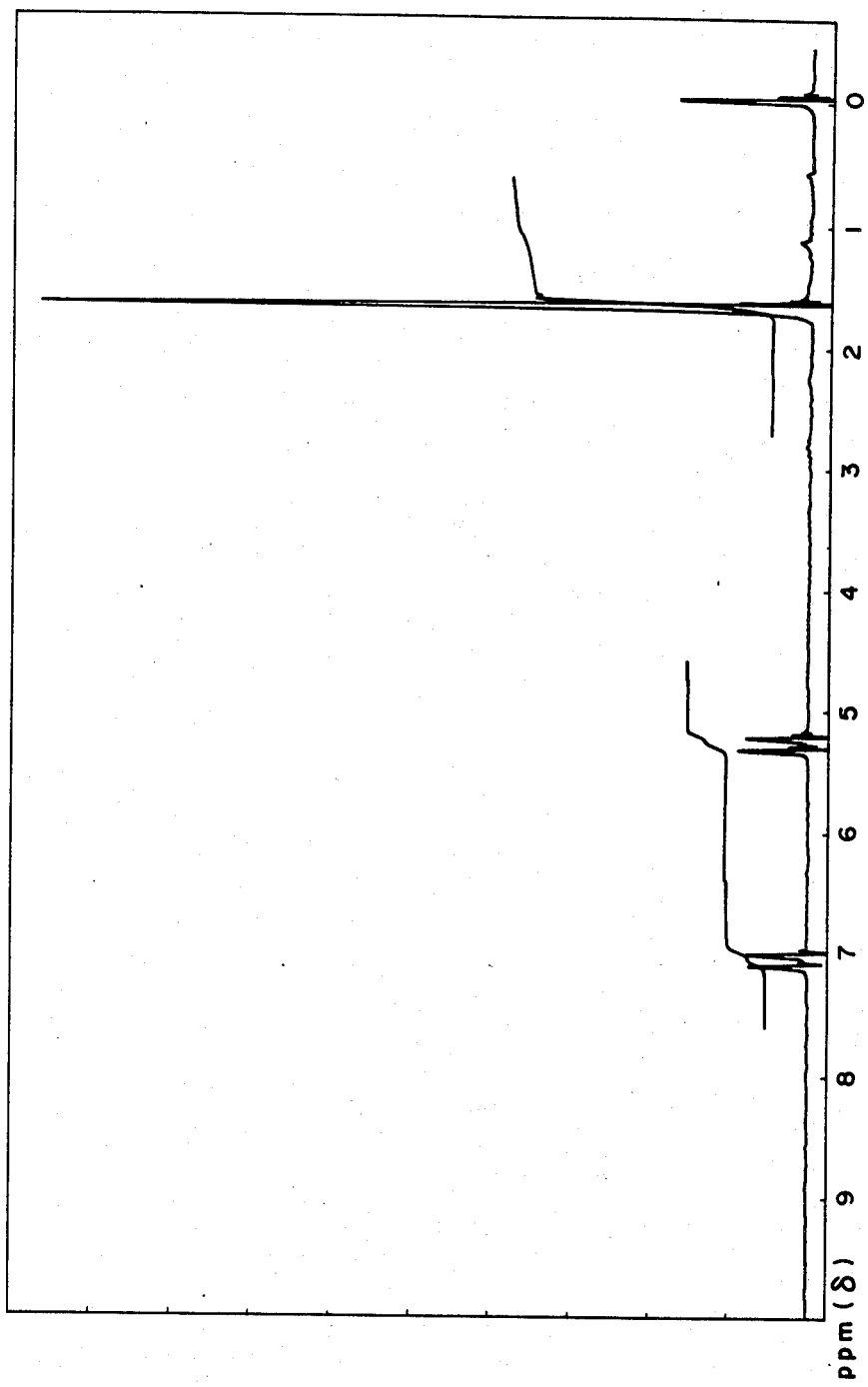

According to the result of high resolution mass spectroscopy of this product, its molecular weight was 128.0483 (calculated value in terms of $C_6H_8O_3$ (M+): 128.0473). Further its infrared absorption spectra and $^1$H NMR spectra are shown in FIG. 1 and FIG. 2, respectively.

IR (CHCl$_3$): 1730, 1620 cm$^{-1}$
NMR (CCl$_4$): 1.70 (6H, s, C$_2$ (CH$_3$)$_2$);
5.28 (1H, d, J=6Hz, C$_5$—H);
7.07 (1H, d, J=6Hz, C$_6$—H)

EXAMPLE 2

Acetone (2.9 g) was added to sufficiently dehydrated toluene (500 ml) and the mixture was heated under reflux in a reaction flask equipped with a reflux condenser. While the reflux was continued, a warm solution obtained by dissolving formyl Meldrum's acid (8.6 g) in toluene (500 ml) on heating was dropwise added over about 2 hours, followed by subjecting the reaction mixture to heating under reflux for additional one hour and then subjecting the resulting reaction mixture to purifying operation in the same manner as in Example 1 to obtain 2,2-dimethyl-1,3-dioxin-4-one (5.3 g, yield 82%).

EXAMPLE 3

Acetone of reagent grade (11.6 g, 200 mmols) and anhydrous aluminum chloride of reagent grade (0.07 g) were added to sufficiently dehydrated toluene of reagent grade (1,000 ml), and the mixture was heated under reflux under the atmospheric pressure. While the reflux was continued, formyl Meldrum's acid (8.6 g, 50 mmols) was small-portion-wise added over 30 minutes. After completion of the addition, the reflux was continued for additional 30 minutes.

The reaction liquid was cooled to room temperature, followed by adding purified water (100 ml), shaking the mixture, allowing it to still standing, separating the resulting toluene layer, saturating the aqueous layer with sodium chloride, twice extracting the resulting solution with an equal volume of toluene, combining the extract solution with the previously separated toluene layer, adding anhydrous magnesium sulfate for drying, filtering off the drying agent, and subjecting the resulting toluene solution to distillation operation in the same manner as in Example 1 to obtain 2,2-dimethyl-1,3-dioxin-4-one (4.8 g, yield 75%).

COMPARATIVE EXAMPLE 1

Acetone (1.74 g, 30 mmols) and formyl Meldrum's acid (2.58 g, 15 mmols) were added to xylene (60 ml), and the mixture was heated under reflux in a flask equipped with a reflux condenser for 30 minutes. The reaction mixture solution was subjected to column chromatography using silica gel as adsorbent and a mixed solvent of n-hexane-diethyl ether (8:1) as developer to separate the objective product, followed by distilling off the developing solvent under reduced pressure to obtain an oily substance (0.60 g, yield 31%).

EXAMPLE 4

Reaction was carried out in the same manner as in Example 1 except that acetone (2.9 g, 50 mmols) was replaced by methyl ethyl ketone of reagent grade (18.0 g, 250 mmols), followed by distilling off excess methyl ethyl ketone and the solvent from the reaction mixture, subjecting the resulting residue to silica gel column chromatography and eluting with a mixed solvent of n-hexane and ethyl acetate (10:1) to obtain an oily substance, which was then subjected to vacuum distillation to obtain a fraction having a boiling point of 60° C. (heating bath temperature)/3 mmHg (5 g, yield 70%). This substance was identified with the objective 2-ethyl-2-methyl-1, 3-dioxin-4-one from the following results of IR spectra and $^1$HNMR spectra:

IR(CHCl$_3$): 1730, 1620 cm$^{-1}$
NMR(CCl$_4$): 1.2 (3H, t, J=7 Hz, CH$_2$—CH$_3$);
1.63 (3H, S, CH$_3$);
2.03(2H, q, J=7 Hz, CH$_2$—CH$_3$);
5.26 (1H, d, J=6Hz, C$_5$—H);
7.10 (1H, d, J=6Hz, C$_6$—H)

COMPARATIVE EXAMPLE 2

Formyl Meldrum's acid (1.72 g, 10 mmols) and methyl ethyl ketone (3.6 g, 50 mmols) were heated under reflux in xylene (20 ml) for 30 minutes, followed by subjecting the resulting reaction mixture to the same purification operation as in Example 4 to obtain the objective 2-ethyl-2-methyl -1, 31 -dioxin-4-one (0.5 g, yield 35%).

REFERENCE EXAMPLE

Preparation of formyl Meldrum's acid

Meldrum's acid (28.4 g, 0.2 mol) was reacted with trimethyl orthoformate (106 g, 1 mol) on heating at 85-95+ C. for 3 hours. After cooling, most part of methoxy methylene Meldrum's acid precipitated. Petroleum ether was further added, followed by filtering off deposited crystals and recrystallizing the crystals from a mixed solvent of chloroform-petroleum ether. Yield: 28 g (75%).

The crystals were sublimated at 120° C. and 0.002 Torr. The resulting crystals had a m.p. of 136°–137° C.

Next, this methoxy methylene Meldrum's acid (25 g, 0.13 mol) was dissolved in chloroform (200 ml), followed by adding 2N-HCl (50 ml), agitating the mixture at room temperature, allowing it to still standing, separating the chloroform layer, saturating the aqueous layer with sodium chloride, extracting the solution with chloroform, combining the extract solution with the previously obtained chloroform solution, drying over anhydrous magnesium sulfate, filtering off the drying agent, and distilling off chloroform under reduced pressure to obtain raw formyl Meldrum's acid as residue, adding ether thereto, filtering off, further washing with ether, vaporizing the remaining ether and recrystallizing the resulting crystals from a mixed solvent of dichloromethanehexane to obtain formyl Meldrum's acid in the form of colorless crystals (20.5 g, yield 89%) having a m.p. of 95°–96° C.

What we claim is:

1. A process for producing 1,3-dioxin-4-one derivatives having a lower alkyl group at 2-position thereof, which process comprises reacting formyl Meldrum's acid with a lower aliphatic carbonyl compound of 2 to 4 carbon atoms in a solvent containing said carbonyl compound at 100° to 120° C., while portionwise adding said acid into said solvent, the total quantity of said acid added being 0.2 mol or less per liter of said solvent.

2. A process according to claim 1 wherein the reaction is carried out under the boiling reflux of said solvent containing said carbonyl compound.

3. A process according to claim 1 wherein said solvent further contains anhydrous aluminum chloride or boron trifluoride as catalyst.

4. A process according to claim 2 wherein said solvent further contains anhydrous aluminum chloride or boron trifluoride as catalyst.

5. A process according to claim 1 wherein said carbonyl compound is acetone.

* * * * *